United States Patent [19]

Makino et al.

[11] Patent Number: 4,814,176

[45] Date of Patent: Mar. 21, 1989

[54] SUSTAINED RELEASE PREPARATION

[75] Inventors: Yuji Makino; Hideo Matugi; Yoshiki Suzuki, all of Hino, Japan

[73] Assignee: Teijin Ltd., Osaka, Japan

[21] Appl. No.: 817,649

[22] Filed: Jan. 10, 1986

[30] Foreign Application Priority Data

| Jan. 11, 1985 | [JP] | Japan | 60-2160 |
| Jun. 4, 1985 | [JP] | Japan | 60-119692 |
| Jun. 24, 1985 | [JP] | Japan | 60-135920 |

[51] Int. Cl.$^4$ .......................... A61K 9/52; A61K 9/22; A61K 9/26
[52] U.S. Cl. .................................. 424/457; 424/468; 424/469; 424/470
[58] Field of Search ................ 424/457, 468, 469, 470

[56] References Cited

U.S. PATENT DOCUMENTS

| 4,404,183 | 9/1983 | Kawata et al. | 424/501 |
| 4,472,376 | 9/1984 | Kamishita | 424/81 |
| 4,501,835 | 2/1985 | Berke | 424/485 |
| 4,536,495 | 8/1985 | Bergwitz et al. | 514/642 |
| 4,572,832 | 2/1986 | Kigasawa et al. | 424/81 |
| 4,606,909 | 8/1986 | Bechgaard et al. | 424/481 |
| 4,642,111 | 2/1987 | Sakamoto et al. | 604/890 |
| 4,666,705 | 5/1987 | DeCrosta et al. | 424/81 |
| 4,681,755 | 7/1987 | Colombo et al. | 424/486 |

*Primary Examiner*—Shep K. Rose
*Attorney, Agent, or Firm*—Sughrue, Mion, Zinn, Macpeak & Seas

[57] ABSTRACT

A sustained release preparation comprising:
(a) chitin, chitosan, or a mixture thereof
(b) anionic polymer compounds such as those having a carboxyl group, a sulfonic acid group, or a group capable of providing the same, and
(c) pharmaceutically active agents.

This sustained release preparation can provide the desired sustained-release or dissolution of the pharmaceutically active agents in human organs irrespective of the acidity (i.e., pH conditions) therein.

8 Claims, No Drawings

SUSTAINED RELEASE PREPARATION

BACKGROUND OF THE INVENTION

1. Field of the Invention

The present invention relates to a sustained release preparation. More specifically, it relates to a sustained release preparation in which a combination of (a) chitin and/or chitosan and (b) an anionic polymer compound is utilized as a sustained-releasing agent.

2. Description of the Related Art

Techniques for the sustained release of preparations have long been studied, to control the dissolution or release and absorption of medicaments from the preparation in human organs upon administration. For example, it is known in the art that medicaments coated by various film-forming substances or medicaments are included or encapsulated in matrices composed of waxes or polymers. However, generally speaking, these known techniques are disadvantageous in that the production processes are complex and the desired sustained release cannot be satisfactorily attained.

Chitin is widely distributed in nature, for example, as a tissue support of crustaceans and insects and chitosan is the deacetylation product thereof. These compounds have heretofore been wasted. However, since these compounds are non-toxic natural polymeric substances, recently attempts have been made to utilize them in various fields. For example, it is reported in S. Miyazaki et al., Chem. Pharm. Bull., 29(10), 3067–3069 (1981) that the suitability of chitin and chitosan as vehicles for the sustained-release of drugs was examined. That is, a drug and chitosan were dissolved in a solvent, followed by distilling off the solvent to thereby prepare a gelled mass. However, this technique is disadvantageous in that the drying must be carried out for a long time and that this technique cannot be applied to medicaments that have a poor resistance to the solvent (e.g., acetic acid in the case of chitosan). It is also reported in Y. Sawayanagi et al., Chem. Pharm. Bull., 30(11), 4213–4215 (1982) that the suitability of chitosan as a vehicle for the sustained release of preparations of water-soluble drugs was examined. According to this reference, chitosan is used together with lactose. Thus, a mixture of chitosan and lactose can form sustained-release preparations in an acidic solution, since chitosan is gelled to encapsulate the medicaments in an acidic solution. However, chitosan acts as a disintegrating agent in a neutral or alkaline solution and, therefore, the encapsulated tablets are immediately disintegrated to rapidly dissolve the medicaments in a neutral or alkaline environment.

Furthermore, it is reported in R. A. Bomstein et al., U.S. Pat. No. 3,833,744 that chitosan is complexed with acidic polysaccharide to yield materials useful as texturizing agents for foods. Although various acidic polysaccharides including alginic acid, pectin, carrageenan, and carboxylmethylcellulose are used together with chitosan as texturizing agents for foods, there is no teaching in this publication that chitosan can form, together with anionic polymer substances, preparations for the sustained-release of medicaments. Furthermore, in Japanese unexamined patent publication (Kokai) No. 55-161804 discloses polyion complexes comprising polycations (e.g., chitosan, glycol chitosan, glyceride chitosan, N-methylglycol chitosan) and polyanion (e.g., carboxymethyl chitosan or its salts), which are usable as microcapsule materials, ultrafiltration membranes, dialysis membranes, conductive or antistatic coating materials, and battery or cell materials. However, there is no teaching in this publication that these polyion complexes can form preparations for the sustained release of medicaments when medicaments are mixed with a combination of (a) chitin and/or chitosan and (b) anionic polymer compounds.

SUMMARY OF THE INVENTION

Accordingly, the objects of the present invention are to eliminate the above-mentioned disadvantages of the prior art and to provide a controlled sustained release preparation capable of providing the desired sustained release or dissolution of medicaments in human organs irrespective of the acidity (i.e., pH conditions) therein.

Other objects and advantages of the present invention will be apparent from the following description.

In accordance with the present invention, there is provided a sustained release preparation comprising:
(a) chitin, chitosan, or a mixture thereof
(b) at least one anionic polymer compound, and
(c) at least one pharmaceutically active agent.

DESCRIPTION OF THE PREFERRED EMBODIMENT

As mentioned above, chitin and/or chitosan usable as the component (a) of the present sustained release preparations are derived from naturally occurring substances. That is, the so-called chitin is 1→4)-2-acetamide-2-deoxy-β-O-glucan having the following structure:

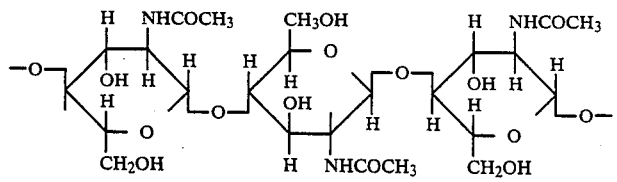

Chitin is widely distributed in nature, for example, as a structural polysaccharide in crustaceans and insects as well as in cells of cumycetes and other microorganisms. Chitosan, i.e., (1→4)-2-amino-2-deoxy-β-D-glucan, which is easily prepared from N-deacetylation of chitin with an alkali, has the following structure:

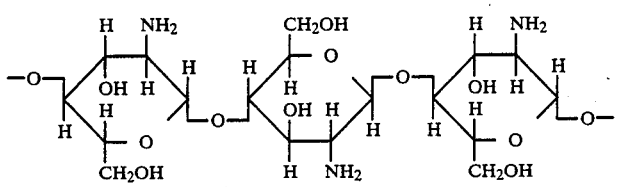

According to the present invention, the use of chitosan is preferable.

The anionic polymer compounds usable as the component (b) in the sustained-release preparations according to the present invention preferably are those having a carboxyl group, a sulfonic acid group, or a group capable of providing a carboxyl group or a sulfonic acid group. These compounds can be used alone or in any mixture thereof.

Typical examples of the anionic polymer compounds having a carboxyl group or a group capable of providing a carboxyl group are carboxyvinyl polymer and the salts thereof, polyacrylic acid and the salts thereof, methoxyethylene-maleic anhydride copolymer and the hydrolyzates thereof, methacrylic acid-methyl methacrylate copolymer, partial methyl esters of vinyl acetate-maleic anhydride copolymer, vinyl acetate-crotonic acid copolymer, carboxymethyl cellulose, alginic acid, pectin, hyaluronic acid and poly-L-glutamic acid.

Typical examples of the carboxylvinyl polymers are cross-linked acrylic acid polymers, preferably having a viscosity of about 1000 to 100,000 cps measured at 25° C. in a 0.2% aqueous solution by a B 8H type rotational viscometer. Examples of such commercially available acrylic acid polymers are Carbopol 934, 940, and 941 manufactured by the B.F. Goodrich Co., Hiviswako 103, 104, and 105 manufactured by Wako Pure Chemical Co., and Zyunron pW 110 and 111 manufactured by Nihon Zyunyaku Co.

The methoxyethylene-maleic anhydride copolymers usable as a component (b) of the present sustained release preparations are those having the general formula:

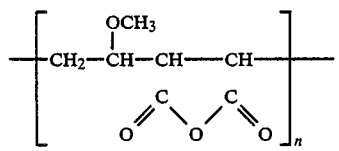

The hydrolyzates of the methoxyethylene-maleic anhydride copolymers having the following general formula:

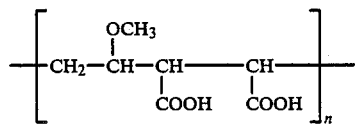

also can be used as a component (b) of the present sustained release preparations. The preferable hydrolyzates are those obtained by hydrolyzing 50% or more, preferably 75% or more, of the maleic anhydride portions to the carboxylic acid groups.

Typical examples of the anionic polymer compounds having a sulfonic acid group or a group capable of providing the same are dextran sulfric acid, carrageenan, heparin, chondroitin sulfric acid, and the salts thereof.

Although there is no limitation to the amount of the component (b) to the component (a) in the sustained release preparations according to the present invention, the preferable formulating ratio is 10 to 1000 parts by weight, more preferably 20 to 500 parts by weight, based on 10 parts by weight of the component (a). When the amount of the component (a) is less than 10 parts by weight based on 100 parts by weight, the shape retentionability of the resultant preparations becomes poor. On the other hand, when the amount of the component (b) is more than 1000 parts by weight based on 100 parts by weight of the component (a), the tackivess thereof to human organs is decreased.

The pharmaceutically active agents usable as the component (c) in the present invention can be any of those agents which are generally required to be frequently administered for maintaining the effective blood concentration or effective local content thereof. Typical examples of such pharmaceutically active agents are as follows.

(1) Antipyretic, Analgesic, or Antiphlogistic

Mefenamic acid, acemetacin, indomethacin, alclofenac, ibuprofen, tiaramide hydrochloride, ketoprofen, diclofenac sodium, sulindac, naproxen, fenbufen, flurbiprofen, mepirizole, and the like.

(2) Antiarrhythmics

Acebutolol hydrochloride, alprenolol hydrochloride, indenolol hydrochloride, oxprenolol hydrochloride, carteolol hydrochloride, propanolol hydrochloride, pindolol, disopyramide, and the like.

(3) Hypotensors

Clonidine hydrochloride, prazosin hydrochloride, captopril, metoprolol tartrate, methyldopa, betanidine sulfate, and the like.

(4) Vasodilator

Etafenone hydrochloride, oxyfedrine hydrochloride, Carbochromen hydrochloride, dilazep dihydrochloride, diltiazem hydrochloride, trimetazidine hydrochloride, verapamil hydrochloride, dipyridamole, isosorbide dinitrate, trapidil, nicorandil, nifedipine, inositol hexanicotinate, isoxsuprine hydrochloride, nicametate citrate, cyclandelate, cinnarizine, and the like.

(5) Antiarteriosclerotics

Clofibrate, simfibrate, elastase, systerol, nicomol, and the like.

(6) Agents for Circulating Systems

Nicardipine hydrochloride, nimodiphine hydrochloride, meclofenoxate hydrochloride, cytochrome C, ifenprodil tartrate, tocopherol nicotinate, pentoxifylline, and the like.

(7) Antitussive expectorants

Clorprenaline hydrochloride, pirbuterol hydrochloride, bitolterol mesilate, salbutanol hemisulfate, terbutaline sulfate, hexoprenaline sulfate, dimemorfan phosphate, ambroxal hydrochloride, L-ethylcystine hydrochloride, trimetoquinol hydrochloride, bromhexine hydrochloride, theophylline, tranilast, and the like.

(8) Ulcer Preventives

Aceglutamide aluminum, L-glutamine, p-(trans-4-aminomethylcyclohexanecarbonyl)-phenylpropionic acid hydrochloride, cetraxate hydrochloride, pirenzepine hydrochloride, gefarnate, cimetidine, glycopyrronium bromide, sulpiride, and prostaglandins such as 17,20-dimethyl-6-oxoprostaglandin $E_1$ methyl ester, 6-oxoprostaglandin $E_1$, 15-methyl-prostaglandin $E_2$, 16-methyl-16-hydroxy-15-dehydroxyprostaglandin $E_1$ methyl ester, 7-thiaprostaglandin $E_1$ methylester, 17,20-dimethyl-7-thiaprostaglandin $E_1$ methyl ester, and the like.

(9) Enzyme Preparations

Chymotrypsin, streptokinase, lysozyme chloride, seaprose, serrapeptase, pronase, bromelains, montease, and the like.

(10) Antimalignant Agents

Methotrexate, carboquone, carmofur, tegaful, fluorouracil, and the like.

(11) Chemotherapeutic Agents

Oxacillin, pheneticillin potassium, amoxicillin, ampicillin, cefalexin, cefradin, and the like.

(12) Antiphlogistic Steroid Agents

Hydrocortisone, prednisolone, triamcinolone, triamcinolone acetanide, dexamethasone, betamethasone, and the like.

(13) Antihistamine Agents

Diphenhydramine hydrochloride, chlorpheniramine maleate, and the like.

(14) Local Anesthetic Agents

Benzocaine and the like.

(15) Mouth Disinfection Agents

Chlorohexidine hydrochloride, hexylresorcin, etacrysin, and the like.

(16) Smooth Muscle Relaxants

Flavoxate hydrochloride and the like.

According to the present invention, the desired sustained release preparations can be prepared by mixing the above-mentioned components (a), (b) and (c), and any optional components, by any conventional method. Before mixing these components, each component is preferably ground or pulverized to a uniform fine powder having a particle size of, for example, about 5 to 500 μm, more preferably 10 to 200 μm. The grinding can be carried out by any conventional grinding machine such as a centrifugal grinder. Furthermore, the grinding may be carried out after mixing the above-mentioned three components. The amount of the pharmaceutically active agents to be formulated into the present sustained release preparation can be varied depending upon, for example, the type of the pharmaceutically active agents and, therefore, may be optionally selected based on, for example, the intensity of the activities.

The sustained-release preparations according to the present invention may be perorally, intraorally, intranasally, or locally administered. Alternatively, the present sustained release preparations may be directly applied to the inside of the tissue. The present sustained release preparations may be in the form of, for example, tablets, granules, grains, powders, dental cones, films, or hard capsules.

These preparations can be prepared by any conventional manner. For example, the resultant mixture may be directly or optionally mixed with any conventional ingredients such as foaming agents, lubricants, binders, colorants, and/or flavors prepared to form powders. Examples of foaming agents are sodium bicarbonate and the like. Examples of such lubricants are talc, stearic acid and the salts thereof, and waxes. Examples of binders are starch, dextrin, tragaconth, gelatin, polyvinylpyrrolidone, hydroxypropylcellulose, and polyvinyl alcohol. Examples of the colorants are tar type dyes such as Sunset Yellow. These ingredients may be incorporated into the preparations, unless such incorporation will adversely affect the sustained-release property thereof.

The present sustained release preparations may be prepared in the form of tablets by directly compression molding a uniform mixture of the compounds (a), (b), and (c), and optional ingredients such as foaming agents, lubricants, binders, or colorants. Furthermore, the mixture may be granulated by any conventional method to form granules. The resultant granules may be further ground to form powders.

These preparations may be administered to human organs in any conventional manner so that the activities of the pharmaceutically active agents contained therein can be sufficiently effected. For example, antipyretic, analgesic, or antiphlogistics, antiarrhythmics, hypotensors, vasodilators, antiarteriosclerotics, agents for circulating systems, antitussive expectorants, ulcer preventives, enzyme preparations, antimalignant agents, chemotherapeutic agents, antiphlogistic steroid agents, antihistamine agents, and the like may be perorally administered. Antiarrhythmics, hypotensors, vasodilators, antiarteriosclerotics, agents for circulating systems, antiphlogistic steroid agents, local anesthetic agents, and mouth disinfection agents may be locally administered intraorally or intranasally. Further, antimalignant agents may be directly applied to the inside of the infected tissue.

According to the present invention, pharmaceutically active agents which must be generally administered frequently to maintain the effective blood concentration or effective local concentration thereof can be advantageously incorporated into the present sustained release preparations. Thus, the desired sustained release of these pharmaceutically active agents can be attained and the administration frequency thereof can be remarkably decreased.

EXAMPLES

The present invention will now be further illustrated in detail by, but is by no means limited to, the following Examples, wherein "parts" are all by weight unless otherwise noted.

EXAMPLES 1 TO 3 AND COMPARATIVE EXAMPLES 1 AND 2

(i) A 43.5 part amount of chitosan, 43.5 parts of carboxyvinyl polymer (i.e., Carbopol 941 available from The B.F. Goodrich Co.), 12.5 parts of indomethacin, and 0.5 parts of magnesium stearate were used to prepare tablets, each having a weight of 200 mg, in a conventional manner (i.e., Example 1). The tablets were prepared by a KBr tablet molding machine and a hydraulic press for an infrared adsorption spectral analysis under a compression pressure of 100 kg for 30 minutes. Thus, flat plate tablets having a diameter of 13 mm were formed.

The tablets thus prepared were evaluated, in terms of the indomethacin dissolution (or release) rate, according to the second method of the dissolution test procedure (i.e., the so-called Paddle method) defined in the Pharmacopoeia of Japan (Tenth edition). The No. 1 test solution having a pH of about 1.2 defined in the Pharmacopoeia of Japan was used. This solution was prepared by adding, to 2.0 g of NaCl, 24.0 ml of diluted hydrochloric acid (i.e., 6 ml of HCl was diluted with water to prepare 100 ml of the diluted hydrochloric acid) and water in an amount such that the total amount became 1000 ml.

The test was carried out as follows:

A 500 ml amount of the test solution kept at a temperature of 37° C. was charged into a vessel provided with an agitator with agitating elements. The agitator was rotated at 100 rpm. One sample tablet was dipped in the center of the vessel and the test solution was sampled with the elapse of time. Thus, the dissolution amounts of indomethacin contained in the tablet were spectrophotometrically determined with time and the dissolution rate was calculated.

Similarly, tablets according to Example 2 comprising 43.5 parts of chitosan, 43.5 parts of pectin, 12.5 parts of indomethacin, and 0.5 parts of magnesium stearate, and tablets according to Example 3 comprising 43.5 parts of chitosan, 43.5 parts of alginic acid, 12.5 parts of indomethacin, and 0.5 parts of magnesium stearate were prepared and the dissolution rates thereof were then evaluated in the same manner as mentioned above.

As comparative examples, tablets according to Comparative Example 1 comprising 43.5 parts of microcrystalline cellulose, 43.5 parts of lactose, 12.5 parts of indomethacin, and 0.5 parts of magnesium stearate, and tablets according to Comparative Example 2 comprising 87 parts of chitosan, 12.5 parts of indomethacin, and 0.5 parts of magnesium stearate were prepared and the evaluation tests thereof were then carried out in the same manner as mentioned above.

The results are as shown in Table 1.

TABLE 1

| Tablet | Dissolution Rate (%) of Tablets | | | | |
|---|---|---|---|---|---|
| | 5 min | 15 min | 30 min | 1 hr | 3 hr |
| Example 1 | — | — | 4 | 10 | 21 |
| Comparative Example 1 | 67 | 98 | 100 | ... | ... |
| Example 2 | — | 7 | 15 | 29 | 48 |
| Example 3 | — | 5 | 19 | 35 | 53 |
| Comparative Example 2 | — | — | 2 | 7 | 19 |

(ii) The tablets prepared above in (i) were evaluated in the same manner as mentioned above, except that a No. 2 test solution having a pH of about 6.8, as defined in the Pharmacopoeia of Japan, was used.

The No. 2 test solution was prepared by adding, to 250 ml of 0.2M $KH_2PO_4$, 118 ml of 0.2N sodium hydroxide and water in an amount such that the total amount became 1000 ml.

The results are as shown in Table 2.

TABLE 2

| Tablet | Dissolution Rate (%) of Tablets | | | | |
|---|---|---|---|---|---|
| | 5 min | 15 min | 30 min | 1 hr | 3 hr |
| Table 1 | — | 1 | 7 | 15 | 38 |
| Comparative Example 1 | 75 | 100 | ... | ... | ... |
| Example 2 | — | 8 | 20 | 35 | 61 |
| Example 3 | — | 10 | 18 | 33 | 59 |
| Comparative Example 2 | 75 | 95 | 100 | ... | ... |

As is clear from the results shown in Tables 1 and 2, the dissolution (or release) rates of indomethacin from the tablets in Examples 1, 2, and 3 according to the present invention were sustained or delayed both in the No. 1 and No. 2 test solutions when compared with that of Comparative Example 1. Furthermore, the dissolution rate of the tablets in Comparative Example 2 was similar to those of the tablets according to the present invention in the No. 1 test solution, but was very fast in the No. 2 test solution when compared with that of the tablets according to the present invention. That is, the dissolution of indomethacin from the tablets according to the present invention was desirably delayed or sustained.

EXAMPLE 4

Tablets each having a weight of 200 mg comprising 2.5 parts of chitosan, 42 parts of carboxyvinyl polymer, 5 parts of propranolol hydrochloride, and 0.5 parts of magnesium stearate were prepared in the same manner as in Example 1.

EXAMPLE 5

Tablets each having a weight of 200 mg comprising 47.5 parts of chitosan, 47 parts of carboxyvinyl polymer, 5 parts of nifedipine, and 0.5 parts of magnesium stearate were prepared in the same manner as in Example 1.

EXAMPLE 6

Tablets each having a weight of 40 mg comprising 50.0 parts of chitosan, 49.5 parts of carboxyvinyl polymer, 0.01 part of triamcinolone acetonide, and 0.5 parts of magnesium stearate were prepared in the same manner as in Example 1.

EXAMPLES 7 TO 10 AND COMPARATIVE EXAMPLES 3 AND 4

In Example 7, 43.5 parts of the hydrolyzate of methoxyethylene-maleic anhydride copolymer (the 95% hydrolyzed product, Gantrez S-99 available from GAF Co., Ltd.), 43.5 parts of chiton, 12.5 parts of indomethacin, and 0.5 parts of magnesium stearate were thoroughly mixed together to obtain the powdery composition (Example 7). Then, tablets each having a weight of 200 mg were prepared from the resultant composition in the same manner as in Example 1.

The tablets thus prepared were evaluated, in terms of the indomethacin dissolution (or release) rate, by using the No. 1 test solution having a pH of 1.2, in the same manner as in Example 1.

Similarly, tablets of Example 8 were prepared in the same manner as in Example 7 except that chitosan was used instead of chitin; tablets of Example 9 were prepared in the same manner as in Example 7 except that methoxyethylene maleic anhydride copolymer (i.e., Gantrez AN-169 available from GAF Co., Ltd.) and chitin were used; and tablets of Example 10 were prepared in the same manner as in Example 7 except that the above-mentioned methoxyethylene-maleic anhydride copolymer and chitosan were used.

The tablets obtained above were subjected to the dissolution test in the same manner as in Example 7.

As comparative examples, tablets of Comparative Example 3 comprising 87.0 parts of the above-mentioned hydrolyzate of methoxyethylene maleic anhydride copolymer, 12.5 parts of indomethacin, and 0.5 parts of magnesium stearate, and tablets of Comparative Example 4 comprising 87.0 parts of the above-mentioned methoxyethylene maleic anhydride copolymer, 12.5 parts of indomethacin, and 0.5 parts of magnesium stearate were prepared and evaluated in the same manner as in Example 7.

The results were as shown in Table 3.

TABLE 3

| No. | Composition (parts) | | | | Dissolution Rate (%) | | | | |
|---|---|---|---|---|---|---|---|---|---|
| | | | | | 5 min | 15 min | 30 min | 1 hr | 3 hr |
| Example 7 | Anionic polymer*1 (43.5) | Chitin (43.5) | Indomethacin (12.5) | Mg stearate (0.5) | — | 2 | 12 | 20 | 35 |
| Example 8 | Anionic polymer*1 (43.5) | Chitosan (43.5) | Indomethacin (12.5) | Mg stearate (0.5) | — | — | 8 | 15 | 26 |
| Example 9 | Anionic polymer*2 (43.5) | Chitin (43.5) | Indomethacin (12.5) | Mg stearate (0.5) | — | 2 | 12 | 20 | 34 |
| Example 10 | Anionic polymer*2 (43.5) | Chitosan (43.5) | Indomethacin (12.5) | Mg stearate (0.5) | — | — | 10 | 15 | 23 |
| Comparative Example 3 | Anionic polymer*1 (87.0) | — | Indomethacin (12.5) | Mg stearate (0.5) | — | 10 | 21 | 36 | 59 |
| Comparative Example 4 | Anionic polymer*2 (87.0) | — | Indomethacin (12.5) | Mg stearate (0.5) | — | 11 | 25 | 43 | 66 |

*1Hydrolyzate of methoxyethylene-maleic anhydride copolymer
*2Methoxyethylene-maleic anhydride

EXAMPLE 11

Tablets each having a weight of 200 mg comprising 42.5 parts of the above-mentioned hydrolyzate of methoxyethylene-maleic anhydride copolymer (i.e., Gantrez S-99), 42 parts of chitosan, 15 parts of propranolol hydrochloride, and 0.5 parts of magnesium stearate were prepared in the same manner as in Example 7.

EXAMPLE 12

Tablets each having a weight of 40 mg comprising 50.0 parts of the above-mentioned hydrolyzate of methoxyethylene-maleic anhydride copolymer, 49.5 parts of chitosan, 0.01 part of triamcinolone acetonide, and 0.5 parts of magnesium stearate were prepared in the same manner as in Example 7.

EXAMPLE 13

Tablets each having a weight of 200 mg comprising 42.5 parts of the above-mentioned methoxyethylene-maleic anhydride copolymer (i.e., Gantrez AN-119), 42 parts of chitosan, 15 parts of propranolol hydrochloride, and 0.5 parts of magnesium stearate were prepared in the same manner as in Example 7.

EXAMPLE 14 AND COMPARATIVE EXAMPLE 5

A 44.5 part amount of chitosan, 40.0 parts of carboxyvinyl polymer (i.e., Carbopol 941 available from The B.F. Goodrich Co., Ltd.), 15.0 parts of nifedipine, and 0.5 parts of magnesium stearate were thoroughly mixed together and #2 hard capsules were prepared therefrom by using a conventional hard capsule filling machine. The amount of the powder filled in the capsule was 200 mg.

The hard capsules obtained above were orally administered, together with 20 ml of water to male Beagle dogs having a body weight of about 10 kg, which had fasted for one night. After the administration, blood samples were taken from a vein of a forepaw with time. The nifedipine blood concentration was determined by ECD type gas chromatography.

Simultaneously, as a comparative example, hard capsules (i.e., #2 hard capsules) each having a filling amount of 200 mg containing 42.5 parts of microcrystalline cellulose, 42.0 parts of lactose, 15.0 parts of nifedipine, and 0.5 parts of magnesium stearate were prepared and evaluated in the same manner as in Example 14.

The nifedipine contents in the blood with the elapse of time obtained in Example 14 and Comparative Example 5 are as shown in Table 4. It is clear from the results of Table 4 that the desired sustained release of nifedipine can be more effectively obtained in the hard capsules of Example 14, when compared to those of Comparative Example 5.

TABLE 4

| Dog | Sex | Body wt. (kg) | Capsule | Nifedipine Concentration in Blood (ng/ml) | | | | | |
|---|---|---|---|---|---|---|---|---|---|
| | | | | 30 min | 1 hr | 2 hr | 4 hr | 8 hr | 16 hr |
| A | ♂ | 10.1 | Example 14 | 59 | 168 | 222 | 170 | 133 | 81 |
| B | ♂ | 9.2 | Example 14 | 81 | 184 | 208 | 149 | 126 | 65 |
| C | ♂ | 9.6 | Comparative Example 5 | 402 | 238 | 107 | 32 | 10 | — |
| D | ♂ | 9.8 | Comparative Example 5 | 356 | 210 | 198 | 40 | 5 | — |

EXAMPLES 15 TO 21

Various hard capsules were prepared in the same manner as in Example 14, except that various anionic polymer compounds listed in Table 5 were used instead of the carboxyvinyl polymer used in Example 14.

These hard capsules were evaluated in the same manner as in Example 14. The nifedipine concentration in the blood with the elapse of time, when the hard capsules were administered to male Beagle dogs, are as shown in Table 5. As is clear from the comparison of the results shown in Table 5 with that of Comparative Example 5 in Table 4, the desired sustained release can be more effectively obtained in the hard capsules of Examples 15 to 21.

TABLE 5

| Example No. | Anionic polymer component | Dog | Sex | Body weight (kg) | Nifedipine Concentration in Blood (ng/ml) | | | | | |
|---|---|---|---|---|---|---|---|---|---|---|
| | | | | | 30 min | 1 hr | 2 hr | 4 hr | 8 hr | 16 hr |
| 15 | Methoxyethylene-maleic anhydride copolymer[*1] | E | ♂ | 9.8 | 70 | 163 | 211 | 155 | 109 | 68 |
| 16 | Sodium polyacrylate[*2] | F | ♂ | 9.6 | 101 | 202 | 237 | 174 | 103 | 50 |
| 17 | Carboxymethyl cellulose[*3] | G | ♂ | 10.5 | 48 | 175 | 193 | 66 | 115 | 44 |
| 18 | Carrageenan[*4] | H | ♂ | 9.3 | 67 | 128 | 156 | 149 | 100 | 63 |
| 19 | Poly-L-glutamic acid[*5] | I | ♂ | 10.8 | 65 | 164 | 138 | 111 | 89 | 59 |
| 20 | Methacrylic acid-Methyl methacrylate copolymer[*6] | J | ♂ | 10.0 | 80 | 152 | 147 | 121 | 110 | 66 |
| 21 | Methacrylic acid-Methyl methacrylate copolymer[*7] | K | ♂ | 9.5 | 49 | 136 | 181 | 106 | 97 | 78 |

[*1]Gantrez AN-169 available from GAF Co., Ltd.
[*2]Available from Wako Pure Chemical Co., Ltd.
[*3]Available from Gotoku Yakuhin Co., Ltd.
[*4]Soageena MW321 available from Mitsubishi Rayon Co., Ltd.
[*5]Available from Fluka A.G.
[*6]Eudragit-L available from Rhon Pharma
[*7]Eudragit-S available from Rhon Pharma

We claim:

1. A sustained release preparation consisting essentially of:
   (a) chitin, chitosan, or a mixture thereof;
   (b) at least one anionic polymer compound, and
   (c) a pharmaceutically effective amount of at least one pharmaceutically active agent,
   wherein (b) is present in said preparation in a ratio of from 10 to 1,000 parts by weight per 100 parts by weight of (a).

2. A sustained release preparation as claimed in claim 1, wherein the anionic polymer compounds are those having a carboxyl group, a sulfonic acid group, or a group capable of providing the same.

3. A sustained release preparation as claimed in claim 1, wherein the anionic polymer compounds are those having a carboxyl group or a group capable of providing the same.

4. A sustained release preparation as claimed in claim 1, wherein the anionic polymer compound is at least one compound selected from the group consisting of carboxyvinyl polymer and the salts thereof, polyacrylic acid and the salts thereof, methoxyethylene-maleic anhydride copolymer and the hydrolyzates thereof, methacrylic acid-methyl methacrylate copolymer, partial methyl esters of vinyl acetate-maleic anhydride copolymer, vinyl acetate-crotonic acid copolymer, carboxymethyl cellulose, alginic acid, pectin, hyaluronic acid, and poly-L-glutamic acid.

5. A sustained release preparation as claimed in claim 1, wherein the pharmaceutically active agent is at least one member selected from the group consisting of antipyretic, analgesic, or antiphlogistics, antiarrhythmics, hypotensors, vasodilators, antiarteriosclerotics, agents for circulatory systems, antitussive expectorants, ulcer preventives, enzyme preparations, antimalignants, chemotherapeutic agents, antiphlogistic steroid agents, antihistamine agents, local anesthetic agents, and mouth disinfection agents.

6. A sustained release preparation as claimed in claim 1 in the form of tablets, granules, grains, powders, dental cones, films, or hard capsules.

7. A method for administering a sustained release preparation according to claim 1 whereby the pharmaceutically active agent contained therein is gradually released.

8. A method as claimed in claim 7, wherein the preparation is perorally, intraorally or intranasally administered.

* * * * *